(12) United States Patent
Kanayama et al.

(10) Patent No.: US 9,651,478 B2
(45) Date of Patent: May 16, 2017

(54) ANALYZER

(75) Inventors: Shoichi Kanayama, Otawara (JP);
Tomoyuki Tada, Yokohama (JP);
Naotada Okada, Yokohama (JP)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 0 days.

(21) Appl. No.: 13/347,172

(22) Filed: Jan. 10, 2012

(65) Prior Publication Data

US 2012/0177538 A1    Jul. 12, 2012

(30) Foreign Application Priority Data

Jan. 12, 2011    (JP) .................................. 2011-003622

(51) Int. Cl.
| | |
|---|---|
| *G01J 3/00* | (2006.01) |
| *G01J 3/04* | (2006.01) |
| *G01N 21/25* | (2006.01) |
| *G01N 3/00* | (2006.01) |
| *G01N 3/04* | (2006.01) |
| *G01J 3/36* | (2006.01) |
| *G01N 21/64* | (2006.01) |

(Continued)

(52) U.S. Cl.
CPC .............. *G01N 21/253* (2013.01); *G01J 3/36* (2013.01); *G01N 3/00* (2013.01); *G01N 3/04* (2013.01); *G01N 21/255* (2013.01); *G01N 30/74* (2013.01); *G01N 35/025* (2013.01); *G01N 2021/0325* (2013.01)

(58) Field of Classification Search
None
See application file for complete search history.

(56) References Cited

U.S. PATENT DOCUMENTS

| | | |
|---|---|---|
| 5,157,454 A | 10/1992 | Oka et al. |
| 5,506,679 A | 4/1996 | Cooper et al. |

(Continued)

FOREIGN PATENT DOCUMENTS

| | | |
|---|---|---|
| CN | 1752739 A | 3/2006 |
| EP | 00303707 A1 | 2/1989 |

(Continued)

OTHER PUBLICATIONS

Extended European Search Report issued Oct. 16, 2012 in Patent Application No. 12150820.4.

(Continued)

*Primary Examiner* — Neil N Turk
(74) *Attorney, Agent, or Firm* — Oblon, McClelland, Maier & Neustadt, L.L.P.

(57) ABSTRACT

The analyzer according to the embodiment comprises an irradiation optical part that irradiates a mixture inside reaction tubes with light from a light source. Moreover, a detection optical part detects light transmitted through the mixture. Moreover, the irradiation optical part comprises a first optical element in which the light source is disposed at the front focal position and that concentrates light from the light source. Moreover, a second optical element guides light transmitted through the first optical element to the reaction tubes. In addition, an incident numerical aperture adjustment member is provided at the rear side of the first optical element and adjusts the numerical aperture when light from the light source is incident on the reaction tubes.

12 Claims, 10 Drawing Sheets

(51) Int. Cl.
*G01N 30/74* (2006.01)
*G01N 35/02* (2006.01)
*G01N 21/03* (2006.01)

(56) References Cited

U.S. PATENT DOCUMENTS

| | | | |
|---|---|---|---|
| 5,786,887 | A | 7/1998 | Ebata et al. |
| 6,020,961 | A | 2/2000 | Moore |
| 7,830,518 | B2 | 11/2010 | Kanayama |
| 7,933,014 | B2 | 4/2011 | Kanayama et al. |
| 2008/0192249 | A1* | 8/2008 | Babichenko et al. ........ 356/318 |
| 2009/0009760 | A1 | 1/2009 | Kanayama et al. |
| 2009/0180120 | A1 | 7/2009 | Kanayama |

FOREIGN PATENT DOCUMENTS

| | | |
|---|---|---|
| JP | 4-38555 | 3/1992 |
| JP | 6-273333 A | 9/1994 |
| JP | 6-341944 | 12/1994 |
| JP | 11-295219 | 10/1999 |
| JP | 2000-180368 | 6/2000 |
| JP | 2001-183290 | 7/2001 |
| JP | 2003-149157 | 5/2003 |
| JP | 2005-49109 | 2/2005 |
| JP | 2005-291726 A | 10/2005 |
| JP | 2008-51822 | 3/2008 |
| JP | 2009-9760 | 1/2009 |
| JP | 2009-180120 | 8/2009 |
| JP | 2009-186461 | 8/2009 |
| JP | 2009-531658 | 9/2009 |
| WO | WO 2007/112212 A2 | 10/2007 |

OTHER PUBLICATIONS

Combined Office Action and Search Report issued Dec. 19, 2013 in Chinese Patent Application No. 201210006886.1 with English translation of categories of cited documents.
Office Action issued May 20, 2014 in Japanese Patent Application No. 2011-003622 filed Jan. 12, 2011.

* cited by examiner

ANALYZER

CROSS-REFERENCE TO RELATED APPLICATION

This application is based upon and claims the benefit of priority from Japanese Patent Application No. 2011-003622, filed Jan. 12, 2011; the entire contents of which are incorporated herein by reference.

FIELD

The embodiment of the present invention relates to an analyzer.

BACKGROUND

Various devices exist as analyzers for analyzing test samples.

For example, automatic analyzers are devices that dispense test samples such as human blood and urine as well as reagents inside reaction tubes, cause them to react at a constant temperature after they are mixed and stirred, and measure changes from the resulting reactions, in order to measure the concentration and/or activity of the measured substance or enzyme inside the test sample.

Colorimetric determination and turbidimetric determination are known as the measurement methods are used in this type of automatic analyzer.

Colorimetric determination refers to a method in which mixtures (reaction solutions in which test samples and reagents are mixed) inside reaction tubes are irradiated with light from a light source (wavelengths of light from the near-ultraviolet band to the near-infrared band) and light obtained through the mixtures is divided into spectra and detected by photodetectors, in order to detect changes (absorbance) in specific wavelength components absorbed by the reaction solution.

Moreover, turbidimetric determination generally irradiates mixtures, in which reagents containing latex particles are mixed and stirred with test samples, using light from the light source. Therefore, turbidimetric determination refers to a method in which light obtained through the mixture is divided into spectra and detected by photodetectors, in order to detect the turbidity (permeability) of the mixture, associated with the agglutination of latex particles.

DETAILED DESCRIPTION

The analyzer according to the embodiments comprises an irradiation optical part that irradiates a mixture inside reaction tubes with light from a light source. Moreover, a detection optical part detects light transmitted through the mixture. Moreover, the irradiation optical part comprises a first optical element in which the light source is disposed at the front focal position and concentrates light from the light source. Moreover, a second optical element guides light transmitted through the first optical element to the reaction tubes. In addition, an incident numerical aperture adjustment member is provided at the rear side of the first optical element and adjusts the numerical aperture when light from the light source is incident into the reaction tubes.

(Device Configuration)

Figure 1:
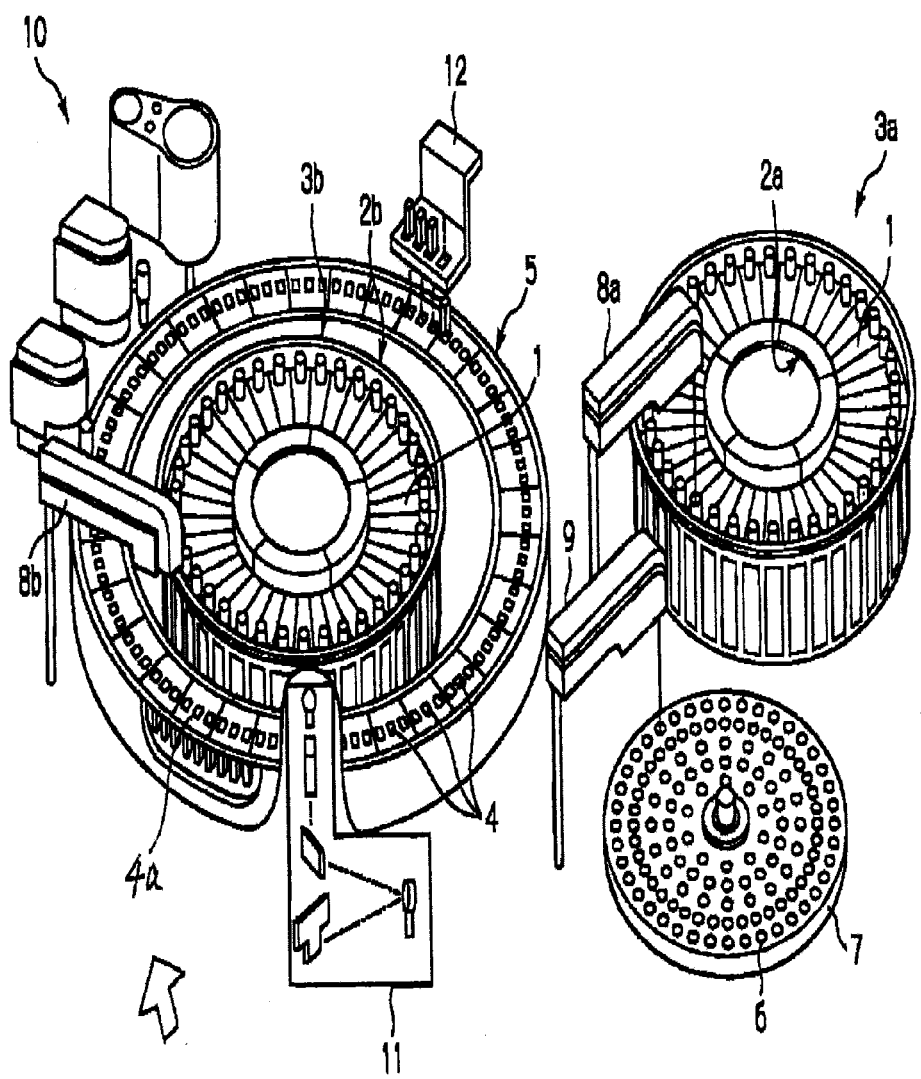
FIG. 1 is an exterior drawing of an automatic analyzer according to the first embodiment and the second embodiment.

First, an explanation is provided regarding the configuration of the automatic analyzer common to both the first embodiment and the second embodiment with reference to FIG. 1. Note that the embodiments relate to the automatic analyzer; however, they are not limited to this. It is also possible to apply the configuration of the present embodiments to various spectroscopic analyzers.

The automatic analyzer comprises reagent bottles 1, reagent racks 2a and 2b, reagent storages 3a and 3b, reaction tubes 4, reaction tube holder 4a, a reaction disk 5, a test sample containers 6, a disk sampler 7, dispensing arms 8a and 8b, a sampling arm 9, a stirring unit 10, a photometric unit 11, and a washing unit 12.

The reagent bottles 1 are containers in which reagents that react with various components of test samples are housed. The reagent rack 2a is provided in the reagent storage 3a in a state in which the plurality of reagent bottles 1 are housed. Similarly, the reagent rack 2b is provided in the reagent storage 3b in a state in which the multiple reagent bottles 1 are housed.

The reaction tubes 4 are containers used when the test sample and the reagent are caused to react. The multiple reaction tubes 4 are disposed in the reaction tube holder 4a at the circumference of the reaction disk 5.

The test sample containers 6 are containers in which test samples are stored. The multiple test sample containers 6 are disposed on top of the disk sampler 7.

The reagents inside the reagent bottles 1 are dispensed into the reaction tubes 4 by the dispensing arm 8a or the dispensing arm 8b. Moreover, the test samples inside the test sample containers 6 are dispensed into the reaction tubes 4 by the sampling arm 9.

The reaction tubes 4 into which the test samples and the reagents are dispensed are moved to the position of the stirring unit 10 by the rotation of the reaction disk 5. The stirring unit 10 is a unit that stirs the reaction tubes 4 in which the test samples and the reagents are contained and mixes the test samples and the reagents.

The stirred reaction tubes 4 are moved to the position of the photometric unit 11. The photometric unit 11 is a unit that irradiates the reaction tubes 4 with light and measures changes in the absorbance, etc., of the mixture of the test sample and the reagent, in order to carry out component analysis of the test sample.

The washing unit 12 is a unit that washes the inside of the reaction tubes 4 after the mixture inside the reaction tubes 4 is disposed of, upon completion of component analysis.

(Configuration of the Photometric Unit 11)

Figure 2:
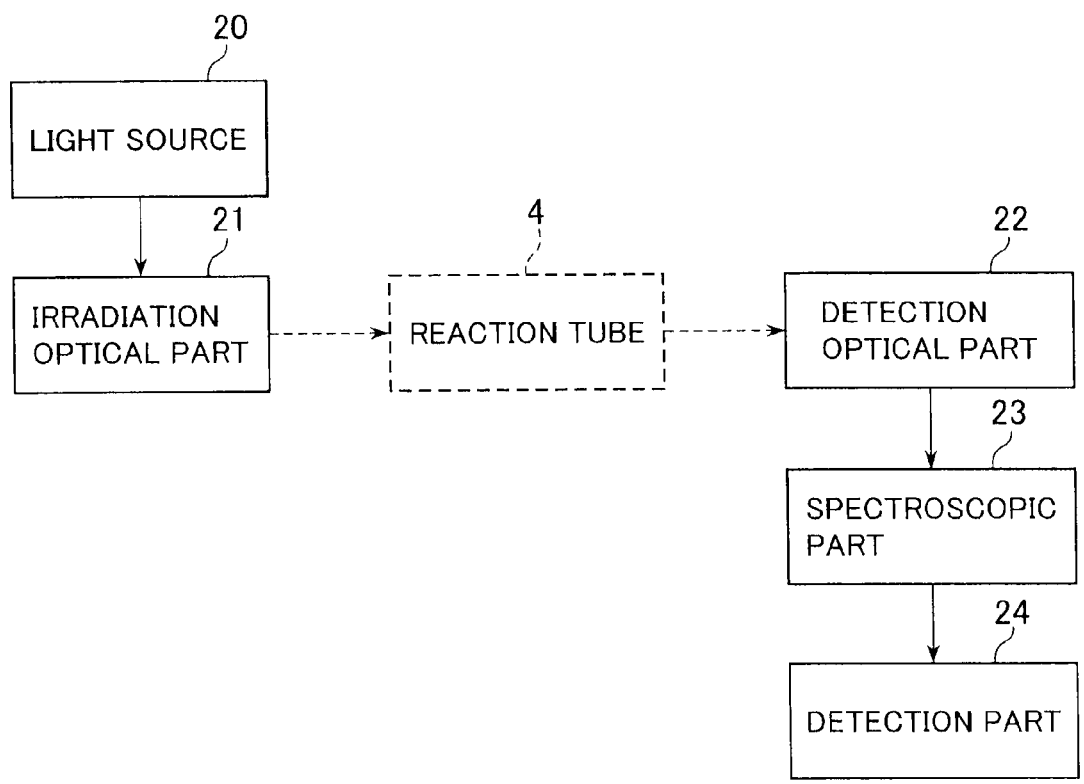
FIG. 2 is a block diagram showing the configuration of a photometric unit of the automatic analyzer according to the first embodiment and the second embodiment.

Next, with reference to FIG. 2, an explanation is provided regarding the configuration of the photometric unit 11 which is common to both the first embodiment and the second embodiment.

The photometric unit 11 comprises a light source 20, an irradiation optical part 21, a detection optical part 22, a spectroscopic part 23, and a detection part 24. Note that in the embodiments, with respect to the optical element, etc. (which will be explained subsequently), disposed in the optical path of the irradiation optical part 21 (or the detection optical part 22), the light source 20 side may be referred to as the "front side" and the detection part 24 side may be referred to as the "rear side."

The light source 20 has a function of generating light that is irradiated to the reaction tubes 4 through the irradiation optical part 21. In the present embodiments, the light source 20 is a white light source and in the measurement, light between the near-ultraviolet region (340 nm) and the near infrared (850 nm) is used.

The irradiation optical part 21 is an optical system for guiding the light generated at the light source 20 to the reaction tubes 4. Moreover, the detection optical part 22 is an optical system for guiding the light transmitted through the reaction tubes 4 to the spectroscopic part 23. The irradiation optical part 21 and the detection optical part 22 will be explained in detail subsequently.

The spectroscopic part 23 has a function of dividing light guided by the detection optical part 22 into spectra by each wavelength. The spectroscopic part 23 includes spectroscopic optical elements such as diffraction grating.

The detection part 24 has a function of detecting the intensity of the light that is divided into spectra by the spectroscopic part 23. The detection part 24 includes photodetectors such as PDAs (Photodiode Arrays).

(First Embodiment)

The automatic analyzer according to the first embodiment is explained in detail with reference to FIG. 3 to FIG. 7.

Figure 3:
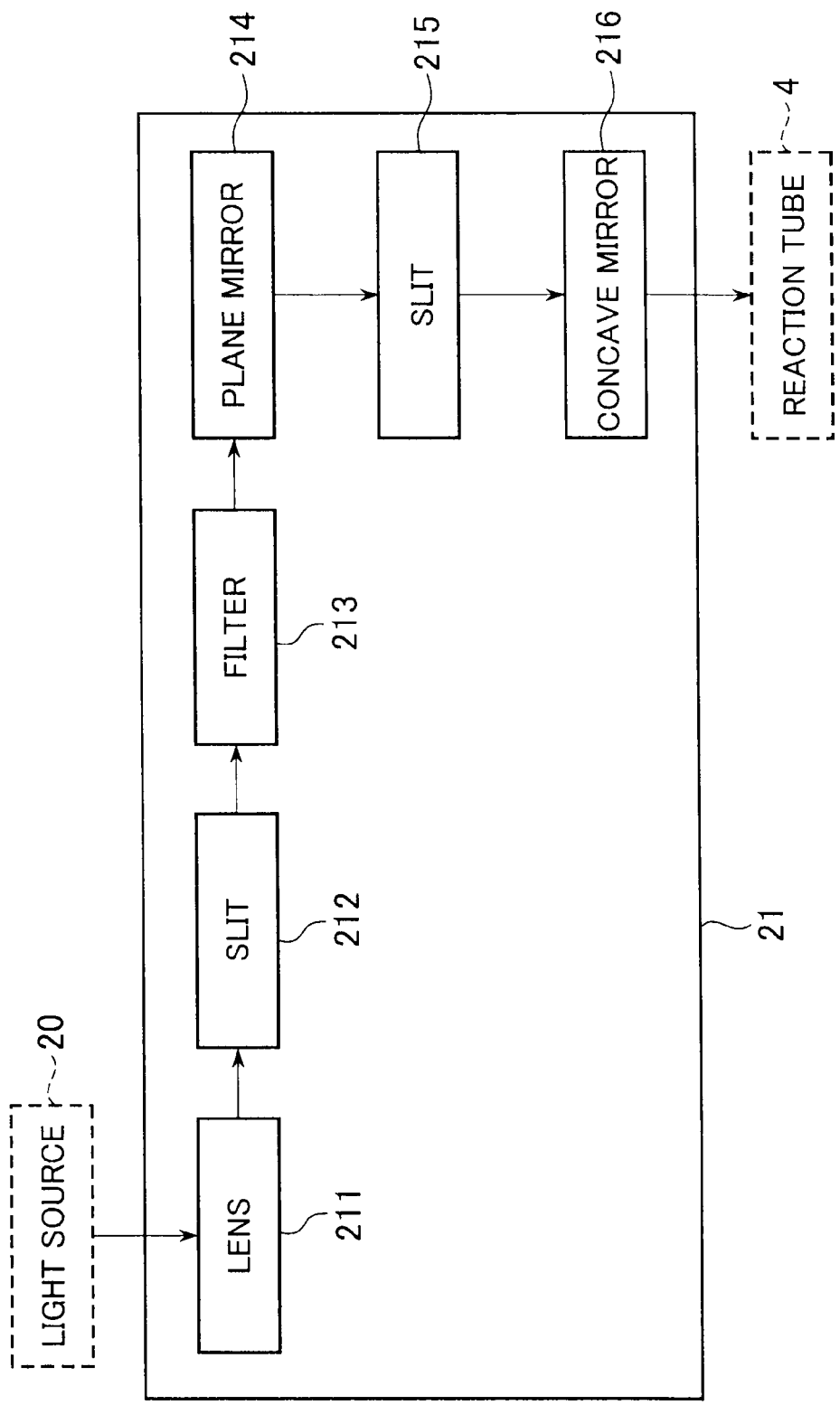
FIG. 3 is a block diagram showing the configuration of an irradiation optical part according to the first embodiment.

As shown in FIG. 3, the irradiation optical part 21 of the photometric unit 11 in the first embodiment comprises a lens 211 (a first optical element), a slit 212 (a first slit), a filter 213, a plane mirror 214, a slit 215 (a second slit), and a concave mirror 216 (a second optical element).

The lens 211 is disposed at the rear side of the light source 20 and is an optical element for concentrating light from the light source 20. The lens 211 is made from an optical lens such as a convex lens.

The slit 212 is disposed at the rear side of the lens 211 and is an aperture for limiting the luminous flux of the light from the lens 211 (light intensity adjustment). The slit 212 may be a transmission type or it may be a reflection type. Moreover, instead of the slit 212, it is also possible to dispose a concave mirror or a plane mirror in order to adjust the luminous flux by means of the reflective effective diameter. In the present embodiment, this may be referred to as the "first slit," including the concave mirror or the plane mirror.

Here, in the present embodiment, the light source 20 is disposed at the front focal position of the lens 211 and the slit 212 is disposed at the rear focal position of the lens 211. Consequently, the light from the light source 20 is turned into light parallel to an optical axis O1 (refer to FIG. 5) of the light source 20 by the lens 211 and only part of this light passes through the slit 212. That is, by limiting some of the light among the light from the light source 20, the size of the beam spot (which will be explained subsequently) and the intensity of light that is incident on the reaction tubes 4 are adjusted.

The filter 213 is an infrared light cut filter that is disposed at the rear side of the slit 212 and absorbs the thermal components of the light passing through the slit 212. Note that the disposition of the filter 213 is not limited to the rear side of the slit 212. For example, it may be provided between the light source 20 and the lens 211.

The plane mirror 214 is a mirror that is disposed at the rear side of the filter 213 and reflects the light passing through the slit 212. In the present embodiment, the optical axis of the light reflected by the plane mirror 214 is referred to as an optical axis O2 (refer to FIG. 5). By reflecting (turning back) the light using the plane mirror 214, it is possible to save space, compared to cases in which the irradiation optical system inside the irradiation optical part 21 (the lens 211, the slit 212, the filter 213, the plane mirror 214, the slit 215, and the concave mirror 216) is disposed in a linear manner.

The slit 215 is disposed at the rear side of the plane mirror 214 and is an aperture for adjusting the numerical aperture (hereinafter may be referred to as the "incident numerical aperture") when the light from the light source 20 is incident into the reaction tube 4, by limiting the luminous flux of the light that is reflected by the plane mirror 214. That is, in the present embodiment, the slit 215 functions as the "incident numerical aperture adjustment member."

The slit 215 may be a transmission type or a reflection type. Moreover, instead of the slit 215, it is also possible to dispose a concave mirror or a plane mirror and adjust the luminous flux by means of the reflective effective diameter. In the present embodiment, it may be referred to as the "second slit," including the concave mirror or the plane mirror.

Note that the slit 215 may be disposed at the rear side of the concave mirror 216. Alternatively, by integrally forming the slit 215 and the concave mirror 216, one optical element may serve as the slit 215 and the concave mirror 216.

The concave mirror 216 is disposed at the rear side of the slit 215 and is an optical element for correcting chromatic aberrations of light passing through the slit 215 and for guiding the corrected light to the reaction tube 4. In the present embodiment, the reasons for using the concave mirror will be explained subsequently.

Figure 4:
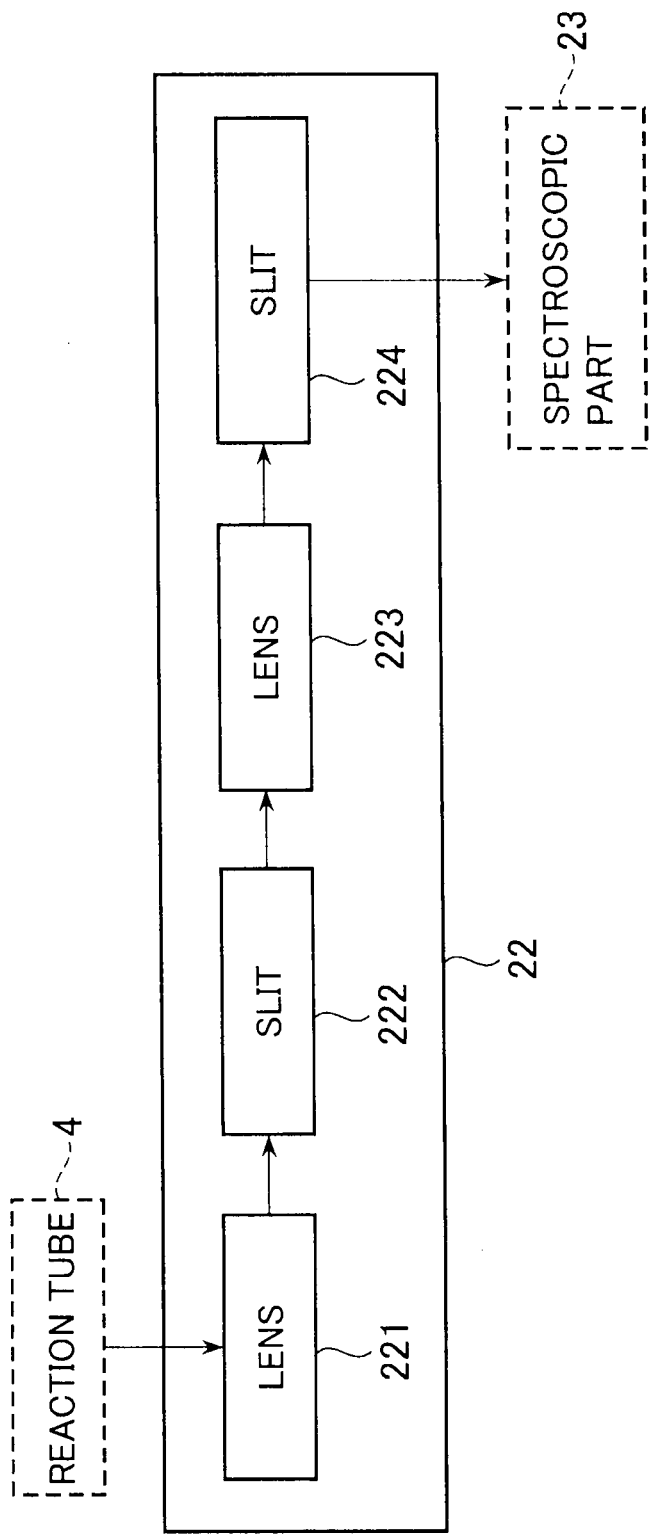
FIG. 4 is a block diagram showing the configuration of a detection optical part according to the first embodiment.

Moreover, as shown in FIG. 4, the detection optical part 22 of the photometric unit 11 according to the first embodiment is constituted from a detection optical system comprising a lens 221 (a third optical element), a slit 222 (a third slit), a lens 223 (a fourth optical element), and a slit 224 (a fourth slit).

The lens 221 is disposed at the rear side of the reaction tube 4 and is an optical element for collimating the light passing through the reaction tube 4. The lens 221 is made from, for example, a collimating lens. The light passing through the reaction tube 4 is adjusted by the lens 221 so as to be in parallel with respect to an optical axis O3 (refer to FIG. 5).

The slit 222 is disposed at the rear side of the lens 221 and is an aperture for adjusting the numerical aperture (hereinafter may be referred to as a "detection numerical aperture") when the light passing through the reaction tube 4 is detected, by allowing some of the light that is collimated with the lens 221 to pass through.

The lens 223 is disposed at the rear side of the slit 222 and is an optical element that concentrates the light passing through the slit 222 and guides it to the slit 224. The lens 223 is made from an optical lens such as a convex lens.

The slit 224 is disposed at the rear side of the lens 223 and is an aperture for allowing some of the light that is concentrated at the lens 223 to pass through. The light passing through the slit 224 is divided into spectra at the spectroscopic part 23 and is detected by the detection part 24 by each wavelength component.

Figure 5:
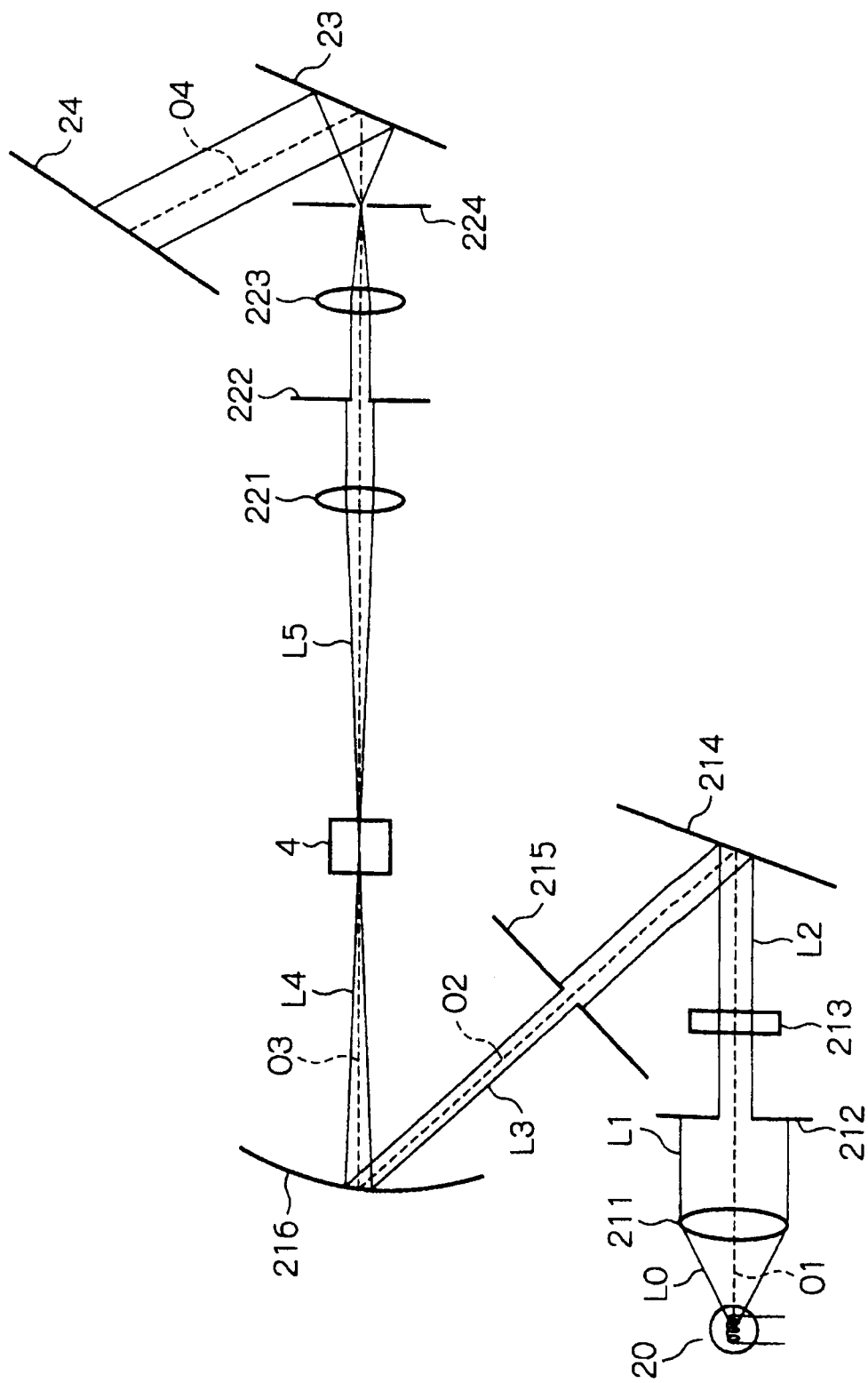
FIG. 5 is a diagram showing the optical system of the photometric unit according to the first embodiment.

Next, an explanation is provided regarding how light progresses in the present embodiment with reference to FIG. 5.

Assuming that the light source 20 is a point light source, light L0 generated by the light source 20 that is disposed at the front focal position of the lens 211 is turned into light L1, which is parallel to the optical axis O1 of the light source 20, by the lens 211. As the light L1 passes through the slit 212, it turns into light L2 in which the luminous flux of the L1 is partially limited. The light L2 is reflected by the plane mirror 214 after it passes through the filter 213. The light L2 that is reflected by the plane mirror 214 reaches the slit 215. The light L2 reached the slit 215 turns into light L3 in which the luminous flux is partially limited, as it passes through this slit 215. Accordingly, the light L3 reaches the concave mirror 216.

Here, the angle at which the light L3 passing through the slit 215 is incident on the concave mirror 216 is preferably equal to or less than 10 degrees with respect to the reflection optical axis O3 of the concave mirror 216. By changing the angle at which the light L3 passing through the slit 215 is incident on the concave mirror 216, the state in which the image of light L4 reflected by the concave mirror 216 is formed (imaging state) changes.

Figure 6:
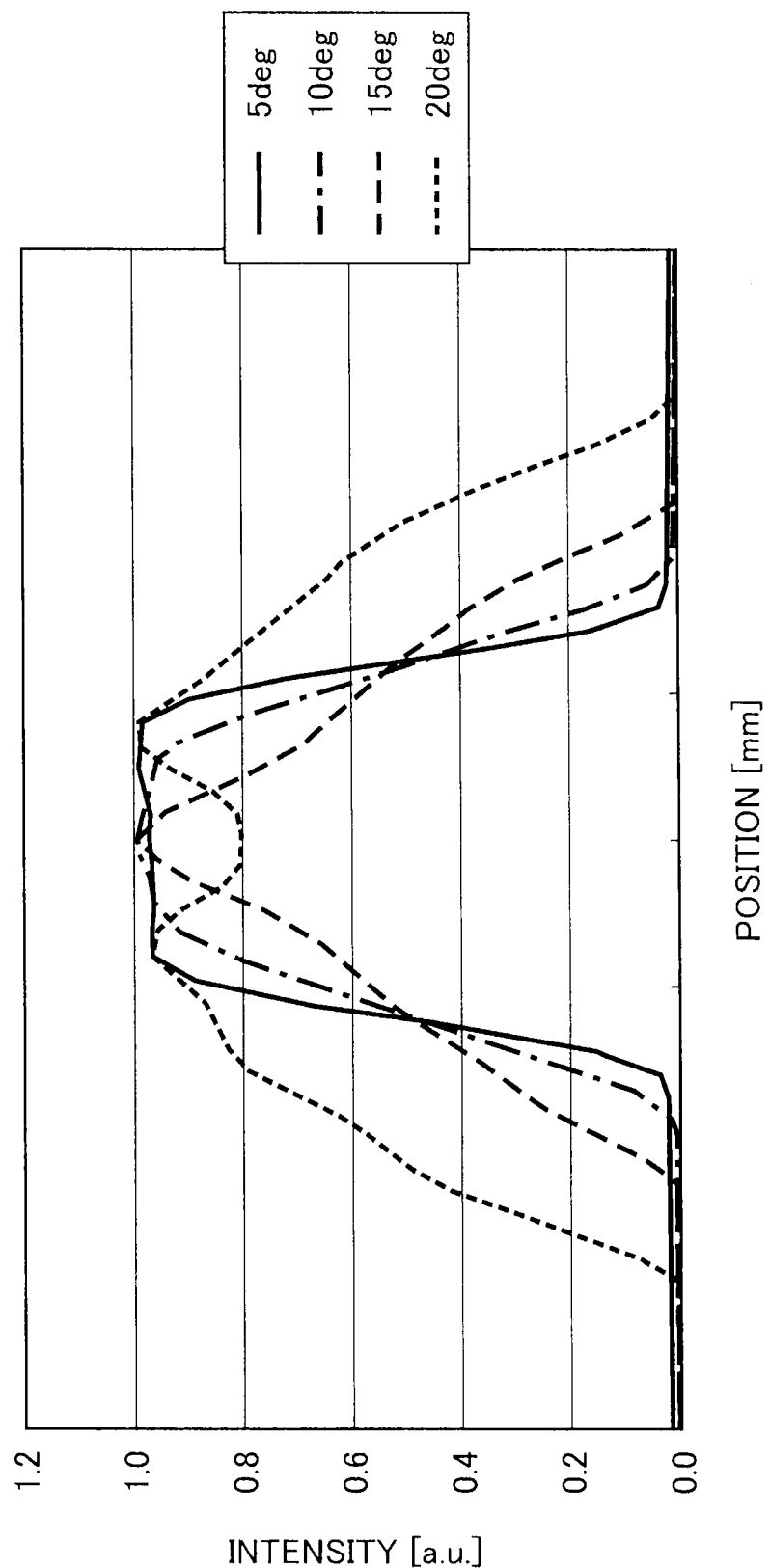
FIG. 6 is a diagram showing the effect according to the first embodiment.

FIG. 6 is a graph showing the intensity distribution at the cross-section of the diameter (the beam spot) of the light L4 that is incident on the reaction tube 4. The vertical axis indicates the intensity and the horizontal axis indicates the position at the cross-section of the beam spot. As is clear from the graph in FIG. 6, if the angle at which the light L3 passing through the slit 215 is incident on the concave mirror 216 (the angle of incidence) is equal to or less than 10 degrees with respect to the reflection optical axis O3 of the concave mirror 216, the light L4 has uniform intensity distribution. Therefore, it is possible to realize an excellent imaging state because light of a uniform intensity can be irradiated to the test sample inside the reaction tube 4.

The light L4 that is reflected by the concave mirror 216 is guided inside the reaction tube 4 and an image is formed inside the reaction tube 4.

Here, generally, when the image is formed using the lenses, there is a problem known as chromatic aberration in which a gap is caused to the imaging state as a result of the wavelength of the light. However, in the present embodiment, the chromatic aberration problem is solved using the concave mirror 216 as the second optical element.

Figure 7:
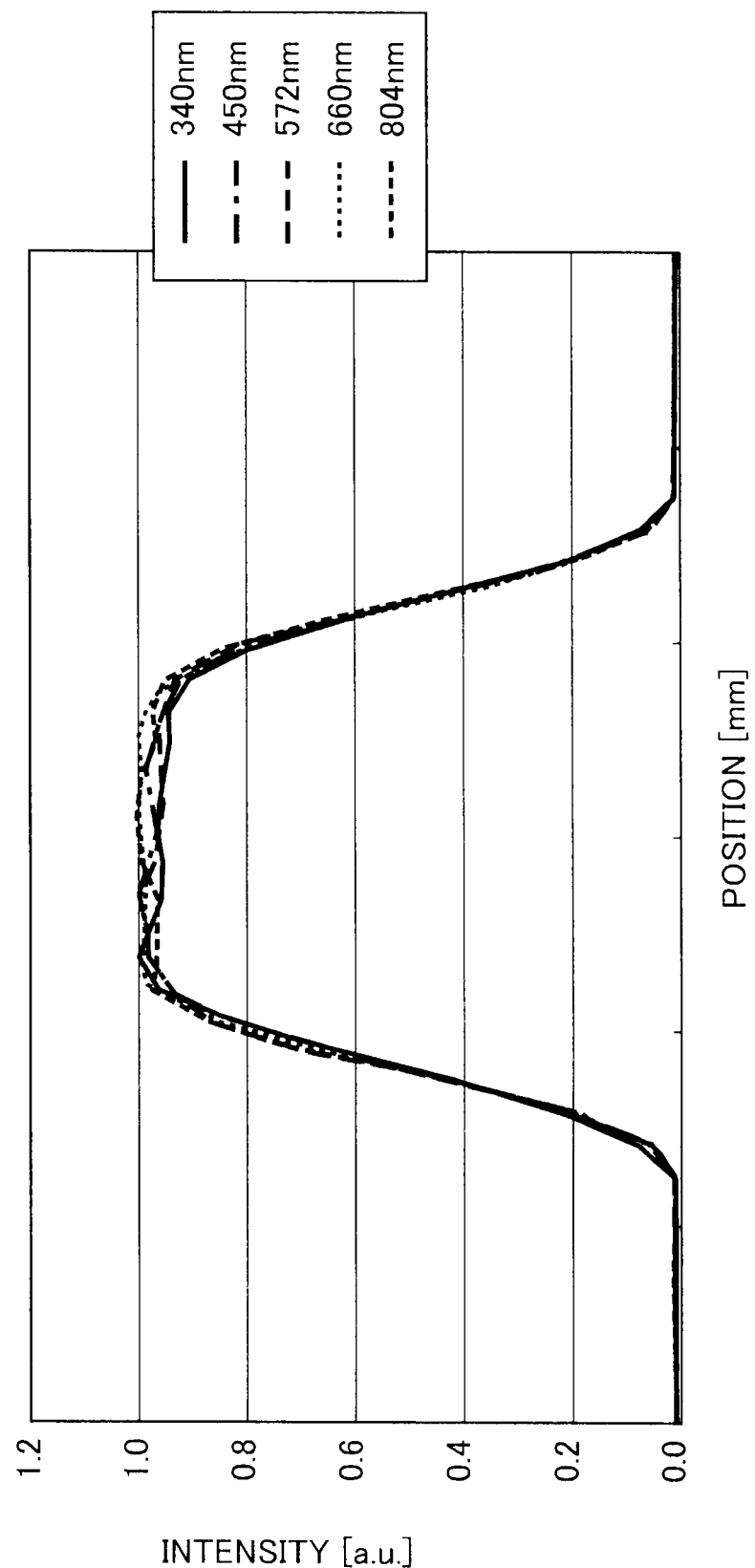
FIG. 7 is a diagram showing the effect according to the first embodiment.

FIG. 7 is a graph showing the results of a simulation of the degree of the chromatic aberration at the image forming position inside the reaction tube 4. The vertical axis indicates the intensity and the horizontal axis indicates the position at the cross-section of the beam spot.

As is clear from this graph, if the concave mirror 216 is used as the second optical element, there is nearly constant intensity from the near-ultraviolet region (340 nm) to near infrared (850 nm). Consequently, it is possible to obtain a uniform imaging state because the chromatic aberration problem is not caused as a result of differences in the wavelengths. Moreover, it is possible to reduce spatial blurs or unevenness of the intensity using this type of light for measurement.

Note that the second optical element may be an element in which the chromatic aberration can be corrected. Therefore, instead of the concave mirror 216, it is also possible to use, for example, an achromatic lens.

Light L5 passing through the reaction tube 4 is collimated by the lens 221 and guided to the spectroscopic part 23 after passing through the slit 222, the lens 223, and the slit 224.

The light L5 reached the spectroscopic part 23 is divided into spectra by each wavelength at the spectroscopic part 23 and detected by the detection part 24 for each wavelength. The test sample is analyzed by calculating the absorbance or the permeability, based on the intensity of the detected light.

Note that reflected light is caused when the light that is divided into spectra at the spectroscopic part 23 is incident on the detection part 24. In order that the reflected light does not return to the spectroscopic part 23, the light incident surface of the detection part 24 is disposed so as to be inclined with respect to an optical axis O4 of the reflection surface of the spectroscopic part 23.

(Action and Effect of the First Embodiment)

In the present embodiment, the second slit has a function of allowing some of the light passing through the first slit to pass through. That is, it is possible to adjust the incident numerical aperture by the second slit.

Moreover, in the present embodiment, the third slit has a function of allowing some of the light passing through the reaction tube 4 to pass through. That is, it is possible to adjust the detection numerical aperture by the third slit.

Moreover, in the present embodiment, if the second slit is integrally formed with the second optical element, it is possible to adjust the incident numerical aperture simply by disposing one optical element.

In this way, according to the present embodiment, by adjusting the incident numerical aperture and the detection numerical aperture, it is possible to reduce the effect of scattered light by turbidimetric determination. Thereby, it is possible to carry out turbidimetric determination efficiently.

Moreover, in the present embodiment, it is possible to prevent chromatic aberration using the concave mirror 216 as the second optical element. Thereby, it is possible to carry out colorimetric determination and turbidimetric determination efficiently.

(Modified Example 1 of the First Embodiment)

In the present modified example, the slit 215 is provided with a variable mechanism (not shown in the figures) that makes it possible to change the width of this slit in order to adjust the incident numerical aperture. By providing this variable mechanism, it is possible to adjust the incident numerical aperture for each measurement item.

Moreover, as is the case with the slit 215, it is possible to provide a variable mechanism to the slit 222 and adjust the detection numerical aperture for each measurement item.

Figure 8:
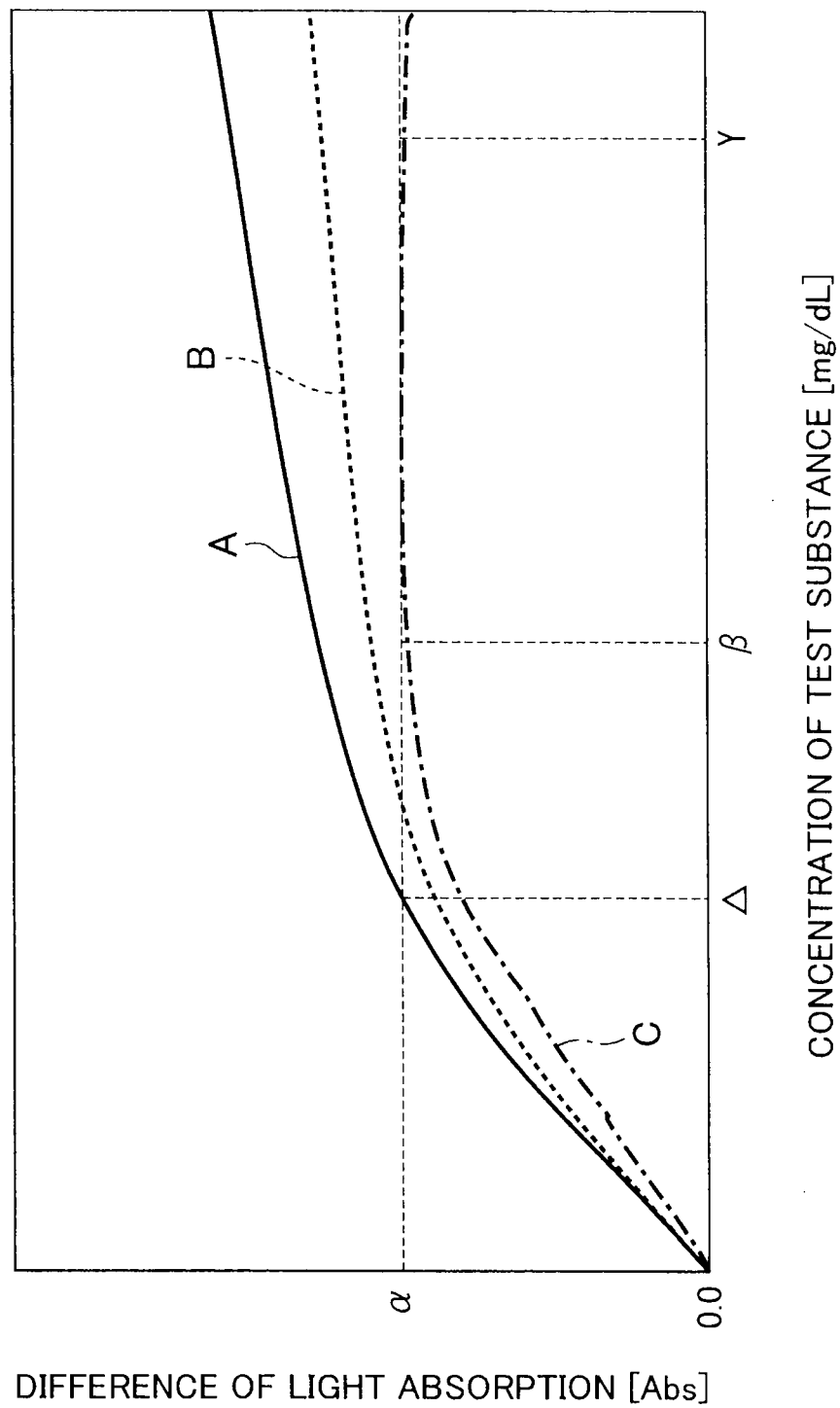
FIG. 8 is a diagram showing the effect according to a modified example of the first embodiment.

FIG. 8 is a graph of the test results showing the comparison results of performance of turbidimetric determination according to the incident numerical aperture (detection numerical aperture). In FIG. 8, the horizontal axis indicates the concentration of test substances and the vertical axis indicates the difference of light absorption detected by the detection part 24. Moreover, in FIG. 8, the symbol A indicates cases in which the numerical aperture is 0.05. In FIG. 8, the symbol B indicates cases in which the numerical aperture is 0.10. In FIG. 8, C indicates cases in which the numerical aperture is 0.25. Note that in FIG. 8, it is assumed that the incident numerical aperture and the detection numerical aperture are equal.

Here, if the concentration of the test substance is calculated from the difference of light absorption, the difference of light absorption preferably retains a proportional relationship with respect to the concentration of the test substance.

For example, in FIG. 8, consider cases of the difference of light absorption α. For cases of C (the numerical aperture 0.25), the concentration value of the test substance may be obtained from β to γ, making it impossible to accurately calculate test substance concentration. In contrast, if the numerical aperture is A (0.05), the test substance concentration is Δ. Therefore, it is possible to uniquely calculate the test substance concentration.

Moreover, the inclination of the graph is larger for cases in which the numerical aperture is A (0.05), compared to cases in which the numerical aperture is B (0.10). That is, the smaller the numerical aperture, the more accurately analysis can be carried out.

(Modified Example 2 of the First Embodiment)

Various effects can be obtained by adjusting the image location of the concave mirror 216. For example, it is possible to reduce the amount of the mixture inside the reaction tube 4 by adjusting the positional relationship of the concave mirror 216 and the reaction tube 4 such that the center of the reaction tube 4 is positioned at the image location of the concave mirror 216. Alternatively, it is possible to reduce detection of the light that is scattered by a scatterer contained in the mixture inside the reaction tube 4 by adjusting the positional relationship of the concave mirror 216 and the reaction tube 4 such that the image location of the concave mirror 216 is positioned at the rear side with respect to the center of the reaction tubes 4.

(Second Embodiment)

Figure 9:
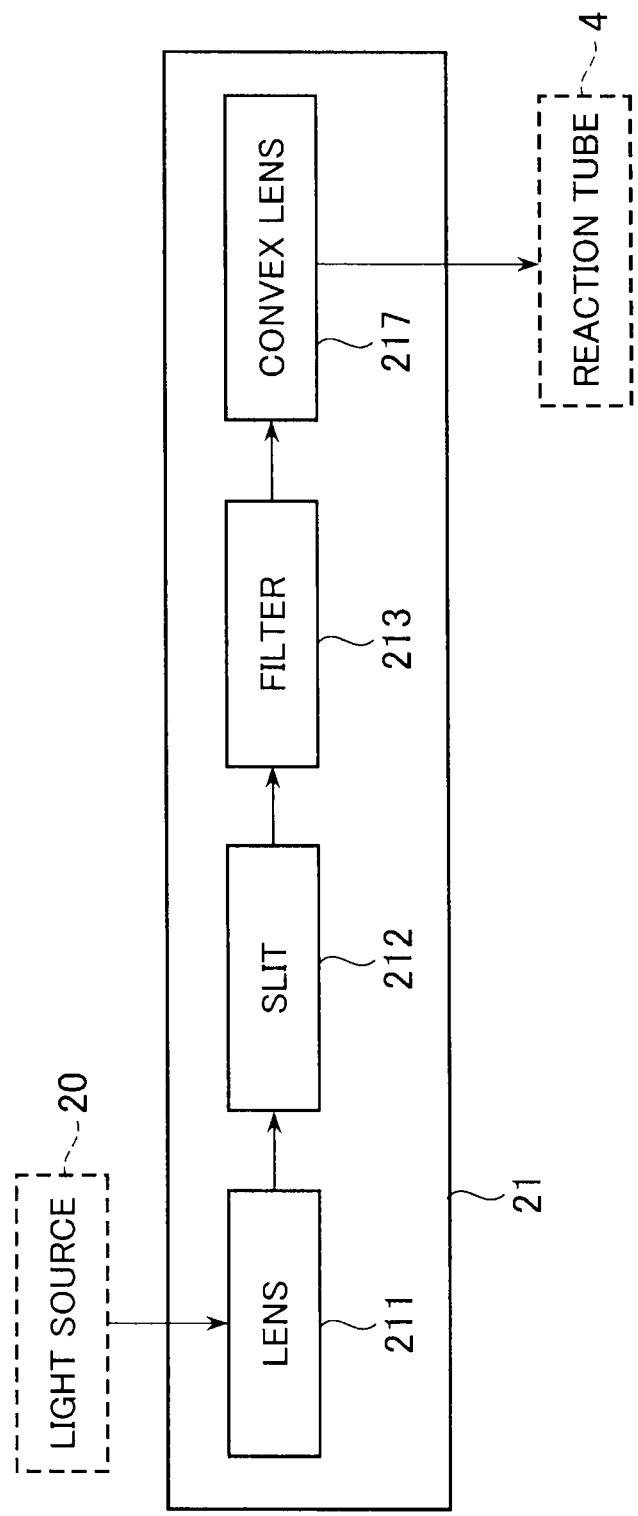
FIG. 9 is a block diagram showing the configuration of the irradiation optical part according to the second embodiment.
Figure 10:
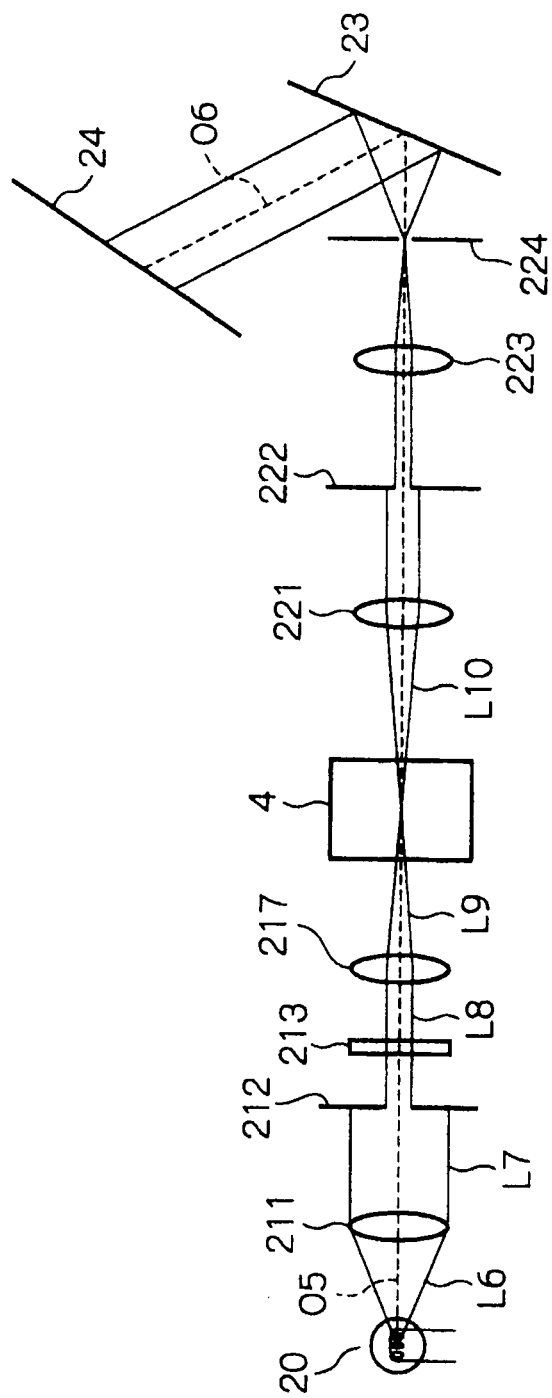
FIG. 10 is a diagram showing the optical system of the photometric unit according to the second embodiment.

Next, an explanation is provided regarding the second embodiment with reference to FIG. 9 and FIG. 10.

As shown in FIG. 9, the irradiation optical part 21 of the photometric unit 11 according to the second embodiment comprises a lens 211 (a first optical element), a slit 212 (a first slit), a filter 213, and a convex lens 217 (a second optical element).

The lens 211 is disposed at the rear side of the light source 20 and is an optical element for concentrating the light from the light source 20. The lens 211 is made from, for example, an optical lens such as a convex lens.

The slit 212 is disposed at the rear side of the lens 211 and is an aperture for limiting the luminous flux of the light from the lens 211 (incident numerical aperture adjustment). That is, in the present embodiment, the slit 212 functions as the "incident numerical aperture adjustment member."

The slit 212 may be a transmission type or it may be a reflection type. Moreover, instead of the slit 212, it is also possible to dispose a concave mirror or a plane mirror in order to adjust the luminous flux be means of the reflective effective diameter. In the present embodiment, this may be referred to as the "first slit," including the concave mirror and/or the plane mirror.

Here, in the present embodiment, the light source 20 is disposed at the front focal position of the lens 211 and the slit 212 is disposed at the rear focal position of the lens 211. Consequently, the light from the light source 20 is turned into light parallel to an optical axis O1 (refer to FIG. 10) of the light source 20 by the lens 211, with only some of this light passing through the slit 212. That is, the incident numerical aperture is adjusted by limiting some of the light among the light from the light source 20.

The filter 213 is an infrared light cut filter that is disposed at the rear side of the slit 212 and absorbs the thermal components of the light passing through the slit 212. Note that the disposition of the filter 213 is not limited to the rear side of the slit 212. For example, it may be provided between the light source 20 and the lens 211.

The convex lens 217 is disposed at the rear side of the slit 212 and is an optical element for guiding the light passing through the slit 212 to the reaction tubes 4. In the present embodiment, the convex lens 217 operates as the second optical element.

Moreover, in the present embodiment, the slit 212 is disposed at the front focal position of the convex lens 217 (at a position away from the convex lens 217 by that focal distance).

As is the case with the first embodiment, the detection optical part 22 is constituted from a detection optical system comprising a lens 221 (a third optical element), a slit 222 (a third slit), a lens 223 (a fourth optical element), and a slit 224 (a fourth slit).

The lens 221 is disposed at the rear side of the reaction tube 4 and is an optical element for collimating the light passing through the reaction tube 4. The lens 221 is made from, for example, a collimating lens. The light passing through the reaction tube 4 is adjusted by the lens 221 so as to be in parallel with respect to the optical axis O5.

The slit 222 is disposed at the rear side of the lens 221 and is an aperture for allowing some of the light that is collimated at the lens 221 to pass through (an aperture for adjusting the detection numerical aperture).

The lens 223 is disposed at the rear side of the slit 222 and is an optical element that concentrates the light passing through the slit 222 and guides it to the slit 224. The lens 223 is made from an optical lens such as a convex lens.

The slit 224 is disposed at the rear side of the lens 223 and is an aperture for allowing some of the light that is concentrated at the lens 223 to pass through. The light passed through the slit 224 is divided into spectra at the spectroscopic part 23 and is detected by the detection part 24 for each wavelength component.

Next, an explanation is provided regarding how light progresses in the present embodiment with reference to FIG. 10.

Light L6 generated by the light source 20 disposed at the front side of the lens 211 is turned into light L7, which is parallel to the optical axis O5 of the light source 20, by the lens 211. As the light L7 passes through the slit 212, it turns into light L8 in which the luminous flux of the L7 is partially limited (in which the incident numerical aperture is adjusted). The light L8 reaches the convex lens 217 after passing through the filter 213.

Light L9 passed through the convex lens 217 is incident on the reaction tube 4.

Light L10 passed through the reaction tube 4 is collimated at the lens 221 and guided to the spectroscopic part 23 after going through the slit 222, the lens 223, and the slit 224. Note that light that is multi-scattered by a scattering medium inside the reaction tube 4 by setting the incident numerical aperture and the detection numerical aperture at the desired values rarely reaches the lens 221.

The light L10 reached the spectroscopic part 23 is divided into spectra at the spectroscopic part 23 by each wavelength and is detected by the detection part 24 for each wavelength. The test sample is analyzed by calculating the absorbance or the permeability, based on the intensity of the detected light.

Note that reflected light is caused when the light that is divided into spectra at the spectroscopic part 23 is incident on the detection part 24. In order that the reflected light does not return to the spectroscopic part 23, the light incident surface of the detection part 24 is disposed so as to be inclined with respect to an optical axis O6 of the reflection surface of the spectroscopic part 23.

(Action and Effect of the Second Embodiment)

As above, in the present embodiment, the incident numerical aperture is adjusted by the slit 212 and the detection numerical aperture is adjusted by the slit 222. It is possible to reduce the detection of the light that is multi-scattered by a scattering medium inside the reaction tube 4 by setting the incident numerical aperture and the detection numerical aperture to desired values, making it possible to carry out turbidimetric determination efficiently.

(Items Common to Both the First Embodiment and the Second Embodiment)

Single-wavelength photometry that uses light of specific wavebands only, and two-wavelength photometry that uses light of two different wavebands and measures their relative changes are known photometric methods of the analyzer. According to the configuration of the first embodiment and the second embodiment, it is possible to efficiently carry out colorimetric determination and turbidimetric determination with either one of these photometric methods.

In the above embodiments, it is also possible to dispose the outgoing radiation end of the fiber at the position in which the light source 20 is disposed. In this case, the light source is provided as a separate body from the photometric unit 11. By guiding the light from this light source through the fiber to inside the irradiation optical part 21, it is possible to obtain the same photometry as the above embodiments.

While certain embodiments have been described, these embodiments have been presented by way of example only, and are not intended to limit the scope of the inventions. Indeed, the novel systems described herein may be embodied in a variety of their forms; furthermore, various omissions, substitutions and changes in the form of the systems described herein may be made without departing from the spirit of the inventions. The accompanying claims and their equivalents are intended to cover such forms or modifications as would fall within the scope and spirit of the inventions.

What is claimed is:

1. An apparatus, comprising:
a reaction tube holder configured to receive reaction tubes;
a light source;
an irradiation optical part that is disposed at a front side of the reaction tube holder, between the light source and the reaction tube holder, and irradiates a mixture including a test substance inside the reaction tubes with light from the light source; and
a detection optical part that is disposed at a rear side of the reaction tube holder, opposite the front side, and detects light transmitted through said mixture,
wherein said irradiation optical part comprises:
a first optical element that concentrates light from said light source which is disposed at a front focal position of the first optical element;
a second optical element that guides light transmitted through said first optical element to said reaction tubes; and
a first numerical aperture adjustment slit that is provided at a rear side of said first optical element, that sets a first aperture for limiting the luminous flux of the light from the first optical element, and that adjusts its size when light from said light source is incident in said reaction tubes, and wherein,
said detection optical part comprises a photodetector and a second numerical aperture adjustment slit that is disposed at a rear side of said reaction tubes, that sets a second aperture for limiting the luminous flux of the light from the reaction tubes, and that adjusts its size,
wherein the first and the second numerical aperture adjustment slits are adjustable such that their sizes are adjusted for each measurement item, and
concentration of the test substance is calculated from a difference of light absorption, wherein the difference of light absorption retains a proportional relationship with respect to the concentration of the test substance; and further comprising:
a third optical element that collimates light transmitted through said reaction tubes;
a third slit that allows part of light transmitted through said third optical element to pass through;
a fourth optical element that concentrates light transmitted through said third slit;
a fourth slit that allows part of light concentrated by said fourth optical element to pass through;
a spectroscopic part that divides light transmitted through said fourth slit into spectra; and
the detection optical part detects at the photodetector light divided into spectra by said spectroscopic part, and
wherein sizes of the third slit and the fourth slit are adjustable for each measurement item.

2. The apparatus according to claim 1, further comprising:
a first slit that is disposed at a rear focal position of said first optical element and allows part of light transmitted through said first optical element to pass through, wherein
said incident first numerical aperture adjustment slit is a second slit that allows part of light transmitted through said first slit to pass through.

3. The apparatus according to claim 2, wherein said second slit is disposed at a front focal position of said second optical element.

4. The apparatus according to claim 2, wherein said second slit is disposed between said second optical element and said reaction tubes.

5. The apparatus according to claim 2, wherein said second slit is integrally formed with said second optical element.

6. The apparatus according to claim 1, wherein said incident first numerical aperture adjustment slit is a first slit that is disposed at a rear focal position of said first optical element and allows part of light transmitted through said first optical element to pass through.

7. The apparatus according to claim 1, wherein the first numerical aperture and the second numerical aperture are equal.

8. The apparatus according to claim 7, wherein the first numerical aperture and the second numerical aperture are equal.

9. The apparatus according to claim 1, wherein the first numerical aperture and the second numerical aperture are both equal to or less than 0.1.

10. The apparatus according to claim 9, wherein the first numerical aperture and the second numerical aperture are both equal to or less than 0.05.

11. The apparatus according to claim 1, wherein said second optical element is a concave mirror.

12. The apparatus according to claim 11, wherein an angle of incidence of light onto said concave mirror is equal to or less than 10 degrees.

* * * * *